US008773002B2

(12) United States Patent
Jin et al.

(10) Patent No.: US 8,773,002 B2
(45) Date of Patent: Jul. 8, 2014

(54) PROBE FOR ULTRASONIC DIAGNOSTIC APPARATUS

(75) Inventors: Gil Ju Jin, Seoul (KR); Jae Yk Kim, Seoul (KR); Jin Woo Jung, Seoul (KR)

(73) Assignee: Samsung Medison Co., Ltd., Kangwon-Do (KR)

( * ) Notice: Subject to any disclaimer, the term of this patent is extended or adjusted under 35 U.S.C. 154(b) by 27 days.

(21) Appl. No.: 13/196,562

(22) Filed: Aug. 2, 2011

(65) Prior Publication Data

US 2012/0056512 A1    Mar. 8, 2012

(30) Foreign Application Priority Data

Sep. 6, 2010    (KR) .................. 10-2010-0086838

(51) Int. Cl.
*H01L 41/08*    (2006.01)
*B06B 1/06*    (2006.01)
*A61B 8/00*    (2006.01)

(52) U.S. Cl.
CPC ............... *B06B 1/06* (2013.01); *A61B 8/4281* (2013.01)
USPC ............... 310/334; 600/437; 600/459

(58) Field of Classification Search
USPC .................. 310/334, 335; 600/437, 459
See application file for complete search history.

(56) References Cited

U.S. PATENT DOCUMENTS

| | | | |
|---|---|---|---|
| 6,038,752 A | 3/2000 | Finsterwald et al. | |
| 6,104,126 A | 8/2000 | Gilmore et al. | |
| 2009/0034370 A1* | 2/2009 | Guo | 367/180 |
| 2010/0324425 A1* | 12/2010 | Kim et al. | 600/459 |
| 2010/0327698 A1* | 12/2010 | Guo | 310/335 |
| 2011/0088248 A1* | 4/2011 | Guo | 29/594 |

FOREIGN PATENT DOCUMENTS

| | | |
|---|---|---|
| EP | 2 025 414 | 2/2009 |
| EP | 2 266 712 | 12/2010 |
| KR | 2010-0056308 A | 5/2010 |
| KR | 2010-0056309 A | 5/2010 |
| KR | 2010-0083090 A | 7/2010 |
| WO | WO 02/40184 | 5/2002 |

OTHER PUBLICATIONS

European Search Report issued in European Patent Application No. 11163291.5 dated Dec. 5, 2011.
Korean Office Action issued in Korean Patent Application No. 10-2010-0086838 dated Jan. 5, 2012.

* cited by examiner

*Primary Examiner* — Jaydi San Martin
(74) *Attorney, Agent, or Firm* — McDermott Will & Emery LLP

(57) ABSTRACT

The present disclosure provides a probe for an ultrasonic diagnostic apparatus. The probe includes a backing layer, a piezoelectric layer disposed on one side of the backing layer, a matching layer disposed on one side of the piezoelectric layer, a signal connector disposed inside the backing layer to transfer a signal to the piezoelectric layer, and a ground connector disposed outside the signal connector. The backing layer, the piezoelectric layer and the matching layer are sequentially disposed and the signal connector is electrically connected to the piezoelectric layer at the other side of the piezoelectric layer. The probe for an ultrasonic diagnostic apparatus includes a stack of the backing layer, the piezoelectric layer and the matching layer, in which the piezoelectric layer is formed to have a certain curvature, thereby achieving performance improvement through minimization of interference from a signal connector and a ground connector.

7 Claims, 6 Drawing Sheets

PROBE FOR ULTRASONIC DIAGNOSTIC APPARATUS

BACKGROUND

1. Technical Field

The present disclosure relates to probes and, more particularly, to a probe for an ultrasonic diagnostic apparatus that generates internal images of a diagnosis object with ultrasound waves.

2. Description of the Related Art

Generally, an ultrasonic diagnostic apparatus refers to a non-invasive apparatus that emits an ultrasound signal from a surface of a patient body towards a target internal organ beneath the body surface and obtains an image of a monolayer or blood flow in soft tissue from information in the reflected ultrasound signal (ultrasound echo-signal). The ultrasonic diagnostic apparatus has been widely used for inspection of the heart, the abdomen, the urinary organs, and in obstetrics and gynecology due to various merits thereof such as small size, low price, real-time image display, and high stability through elimination of radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

The ultrasonic diagnostic apparatus includes a probe which transmits an ultrasound signal to a diagnosis object and receives the ultrasound echo-signal reflected therefrom to obtain ultrasound images of the diagnosis object.

The probe includes a transducer, a case open at an upper end thereof, a cover coupled to the open upper end of the case to directly contact the surface of the diagnosis object, and the like.

The transducer includes a piezoelectric layer in which a piezoelectric material converts electrical signals into sound signals or vice versa while vibrating, a matching layer reducing a difference in sound impedance between the piezoelectric layer and a diagnosis object to allow as much of the ultrasound waves generated from the piezoelectric layer to be transferred to the diagnosis object as possible, a lens layer focusing the ultrasound waves, emitted from the piezoelectric layer, onto a predetermined point, and a backing layer preventing the ultrasound waves from traveling in a rearward direction of the piezoelectric layer to prevent image distortion.

The piezoelectric layer includes a piezoelectric member and electrodes provided to upper and lower ends of the piezoelectric member, respectively. Further, a printed circuit board (PCB) is bonded to the piezoelectric layer. The PCB is formed with wire electrodes connected to the electrodes of the piezoelectric layer to transfer a signal to the piezoelectric layer. The PCB is connected to the piezoelectric layer by connecting the wire electrodes of the PCB to the electrodes of the piezoelectric layer.

It should be noted that the above description is provided for understanding of the background art and is not a description of a well-known conventional technique to which the present disclosure pertains.

The probe for an ultrasonic diagnostic apparatus generally includes a planar piezoelectric layer and employs a curved lens. When manufacturing the probe for an ultrasonic diagnostic apparatus, the electrodes must be manually connected to the piezoelectric layer, thereby increasing manufacturing time and deteriorating performance of the probe due to low durability and non-uniformity at connected portions. Therefore, there is a need for an improved probe for an ultrasonic diagnostic apparatus.

BRIEF SUMMARY

The present disclosure provides a probe for an ultrasonic diagnostic apparatus which may employ a planar lens and is configured to prevent deterioration in performance caused by connection failure between a piezoelectric layer and electrodes.

In accordance with one aspect, a probe for an ultrasonic diagnostic apparatus includes: a backing layer; a piezoelectric layer disposed on one side of the backing layer; a matching layer disposed on one side of the piezoelectric layer; a signal connector disposed inside the backing layer to transfer a signal to the piezoelectric layer; and a ground connector disposed outside the signal connector, wherein the backing layer, the piezoelectric layer and the matching layer are sequentially disposed and the signal connector is electrically connected to the piezoelectric layer at the other side of the piezoelectric layer.

The piezoelectric layer may include a convex piezoelectric portion convexly formed towards the piezoelectric layer.

The backing layer may be provided with backing layer electrodes, the piezoelectric layer may be provided with a piezoelectric layer electrode contacting the backing layer electrodes, the matching layer may be provided with a matching layer electrode contacting the piezoelectric layer electrode, and an insulator may be provided between the backing layer electrodes to divide the backing layer electrodes into first and second backing layer electrodes. The signal connector and the ground connector may be connected to the first and second backing layer electrodes, respectively, and the signal connector and the ground connector may be disposed in the backing layer and extend in a different direction than the piezoelectric layer.

The backing layer may be provided with backing layer electrodes, the piezoelectric layer may be provided with a piezoelectric layer electrode, which surrounds the piezoelectric layer such that one side of the piezoelectric layer electrode contacts the backing layer electrodes and the other side of the piezoelectric layer electrode contacts the matching layer, and an insulator may be provided between the backing layer electrodes to divide the backing layer electrodes into first and second backing layer electrodes. The signal connector and the ground connector may be connected to the first and second backing layer electrodes, respectively, and the signal connector and the ground connector may be disposed in the backing layer and extend in a different direction than the piezoelectric layer.

The matching layer may include a convex matching portion convexly formed corresponding to a shape of the convex piezoelectric portion. The probe may further include a lens disposed outside the matching layer and formed at one side thereof with a lens convex portion convexly formed corresponding to a shape of the convex matching portion. In one embodiment, the other side of the lens opposite the lens convex portion is a planar surface. In another embodiment, the other side of the lens opposite the lens convex portion is convex in a different direction from the lens convex portion.

The signal connector and the ground connector may be disposed only inside the backing layer.

BRIEF DESCRIPTION OF THE DRAWINGS

The above and other features and advantages of the present disclosure will become apparent from the following description of exemplary embodiments given in conjunction with the accompanying drawings, in which.

DETAILED DESCRIPTION

Exemplary embodiments of the present disclosure will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the present disclosure into account and can be changed according to the custom or intention of users or operators. Therefore, definition of the terms should be made according to the overall disclosures set forth herein.

Figure 1:
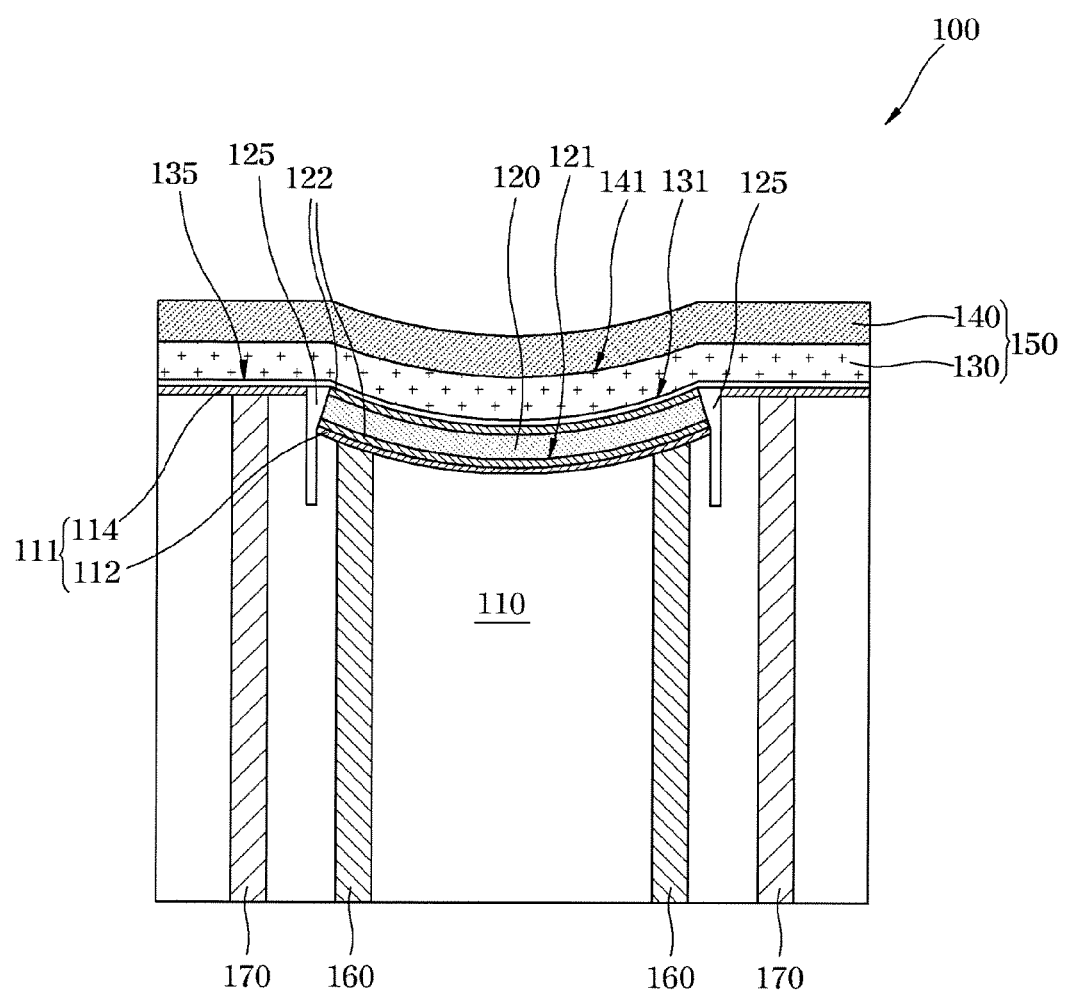
FIG. 1 is a side sectional view of a probe for an ultrasonic diagnostic apparatus according to one exemplary embodiment of the present disclosure.

FIG. 1 is a side sectional view of a probe for an ultrasonic diagnostic apparatus according to one exemplary embodiment of the present disclosure.

Referring to FIG. 1, a probe 100 for an ultrasonic diagnostic apparatus according to one exemplary embodiment includes a backing layer 110, a piezoelectric layer 120, a matching layer 150, a signal connector 160, and a ground connector 170.

The backing layer 110 is disposed on one side of the piezoelectric layer 120 described below. The backing layer 110 suppresses vibration of the piezoelectric layer 120 to reduce the pulse width of ultrasound waves and blocks the ultrasound waves from traveling in a rearward direction of the piezoelectric layer 120 to prevent image distortion. In this embodiment, the backing layer 110 is formed with backing layer electrodes 111, which are divided into first and second backing layer electrodes 112, 114 by an insulator 125 described below.

The piezoelectric layer 120 generates ultrasound waves using a resonance phenomenon. The piezoelectric layer 120 includes a piezoelectric convex portion 121, which is convex towards the backing layer 110. The piezoelectric convex portion 121 may have the same width as that of the backing layer 110 or a smaller width than the backing layer 110. As such, the piezoelectric convex portion 121 may be modified in various ways. In this manner, the piezoelectric layer 120 has a curvature, whereby a planar lens may be applied instead of a curved lens to the probe according to the embodiment. Consequently, a high frequency probe may also use a planar lens by adopting the structure of the probe according to the embodiment. The piezoelectric layer 120 is formed with a piezoelectric layer electrode 122 which contact the backing layer electrodes 111.

The matching layer 150 is disposed on the other side of the piezoelectric layer 120. The matching layer 150 matches sound impedances between the piezoelectric layer 120 and a diagnosis object to allow as much of the ultrasound signals generated from the piezoelectric layer 120 as possible to be transferred to the diagnosis object. In this embodiment, the matching layer 150 includes a first matching layer 130 and a second matching layer 140, which are made of different materials such that sound impedance changes stepwise from the piezoelectric layer 120 to the diagnosis object. The matching layer 150 includes matching convex portions 131, 141, each of which is convexly formed corresponding to the shape of the piezoelectric convex portion 121. In this embodiment, the matching layer 150 is provided with a matching layer electrode 135 which contact the piezoelectric layer electrode 122.

The backing layer 110, the piezoelectric layer 120 and the matching layer 150 are sequentially disposed adjacent to each other to prevent the signal connector 160 or ground connector 170 from being disposed therebetween. In this manner, the backing layer 110, the piezoelectric layer 120 and the matching layer 150 are stacked on one another, so that interference from the signal connector 160 or ground connector 170 can be minimized, thereby improving performance of the probe 100.

The signal connector 160 is disposed inside the backing layer 110 and transfers a signal to the piezoelectric layer 120. The signal connector 160 is electrically connected to the piezoelectric layer 120 at the other side of the piezoelectric layer 120, as shown in FIG. 1. In this embodiment, the signal connector 160 is connected to the first backing layer electrode 112. The signal connector 160 is disposed inside the backing layer 110 and extends in a different direction than the piezoelectric layer 120. For example, the signal connector 160 extends from the first backing layer electrode 112 in a downward direction of the backing layer 110 with reference to FIG. 1.

The ground connector 170 is disposed outside the signal connector 160. In this embodiment, the ground connector 170 is disposed inside the backing layer 110 and extends in a different direction than the piezoelectric layer 120. For example, the ground connector 170 is connected to the second backing layer electrode 114 and extends from the second backing layer electrode 114 in the downward direction of the backing layer 110 with reference to FIG. 1.

It is desirable that the signal connector 160 and the ground connector 170 be disposed only inside the backing layer 110 so as not to interfere with ultrasound waves generated from the piezoelectric layer 120. As such, the signal connector 160 and the ground connector 170 are disposed inside the backing layer 110, thereby achieving improvement in performance of the probe 100. Further, the signal connector 160 and the ground connector 170 may include printed circuit boards (PCB) or other components capable of supplying a signal or electric power. As such, the signal connector 160 and the ground connector 170 may be modified in various manners. Operation and behavior of the signal connector 160 and the ground connector 170 are well known in the art, and a detailed description thereof will thus be omitted herein.

The insulator 125 is provided between the backing layer electrodes 111 to divide the backing layer electrodes 111 into the first and second backing layer electrodes 112, 114. The signal connector 160 is connected to the first backing layer electrode 112 and the ground connector 170 is connected to the second backing layer electrode 114. The insulator 125 may consist of insulator members separated from each other to divide the backing layer electrodes 111 into the first backing layer electrode 112 connected to the signal connector 160 and the second backing layer electrode 114 connected to the ground connector 170. Alternatively, an insulation material for the insulator 112 may be interposed between the first and second backing layer electrodes 112, 114. As such, the insulator 125 may be modified in various manners.

Figure 2:
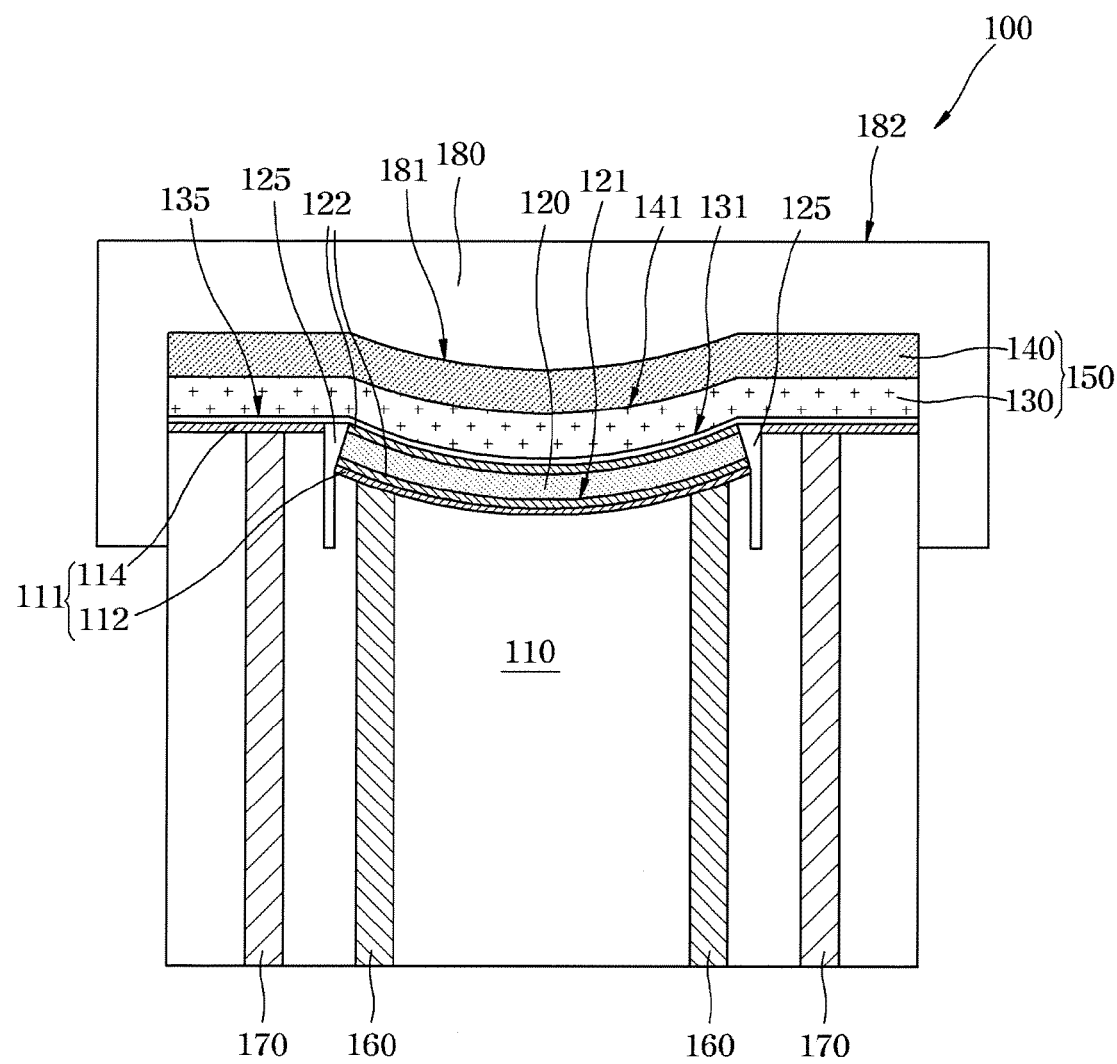
FIG. 2 is a side sectional view of a lens mounted on the probe of FIG. 1.
Figure 3:
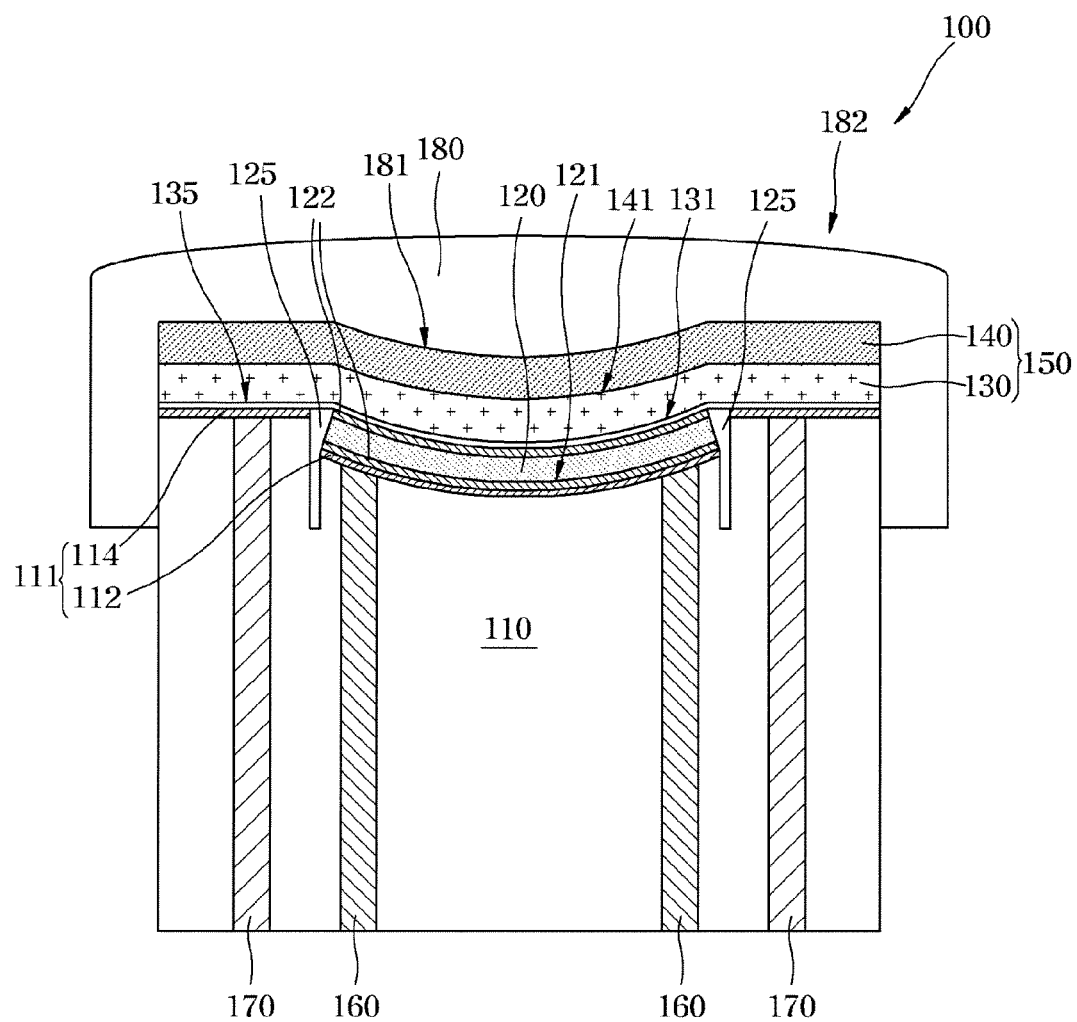
FIG. 3 is a side sectional view of a different lens mounted on the probe of FIG. 1.

FIG. 2 is a side sectional view of the probe of FIG. 1, which includes a lens mounted thereon, and FIG. 3 is a side sectional view of the probe for an ultrasonic diagnostic apparatus of FIG. 1, which includes a lens different from the lens of FIG. 2. Referring to FIG. 2, the probe 100 according to the embodiment further includes a lens 180 mounted on the matching layer 150. The lens 180 includes a lens convex portion 181 which is convexly formed corresponding to the shape of the matching convex portions 131, 141. In one embodiment, one side of the lens 180 is convex towards the matching layer 150 to form the lens convex portion 181 and the other side of the lens 180 opposite the lens convex portion 181 is a planar surface. Thus, the probe 100 according to the embodiment enables application of the planar lens even in the case where a curved lens cannot be applied. Specifically, since the probe according to the embodiment can decrease the thickness of the lens, it is possible to improve sensitivity by inhibiting ultrasonic attenuation caused by the lens thickness and to prevent a problem of frequency drop. Consequently, the probe according to the embodiment may be used as a high frequency probe.

In another embodiment, the other side 182 of the lens 180 opposite the lens convex portion 181 may be convex in a different direction from the lens convex portion 181, as shown in FIG. 3. As such, the lens 180 may be modified in various manners.

Figure 4:
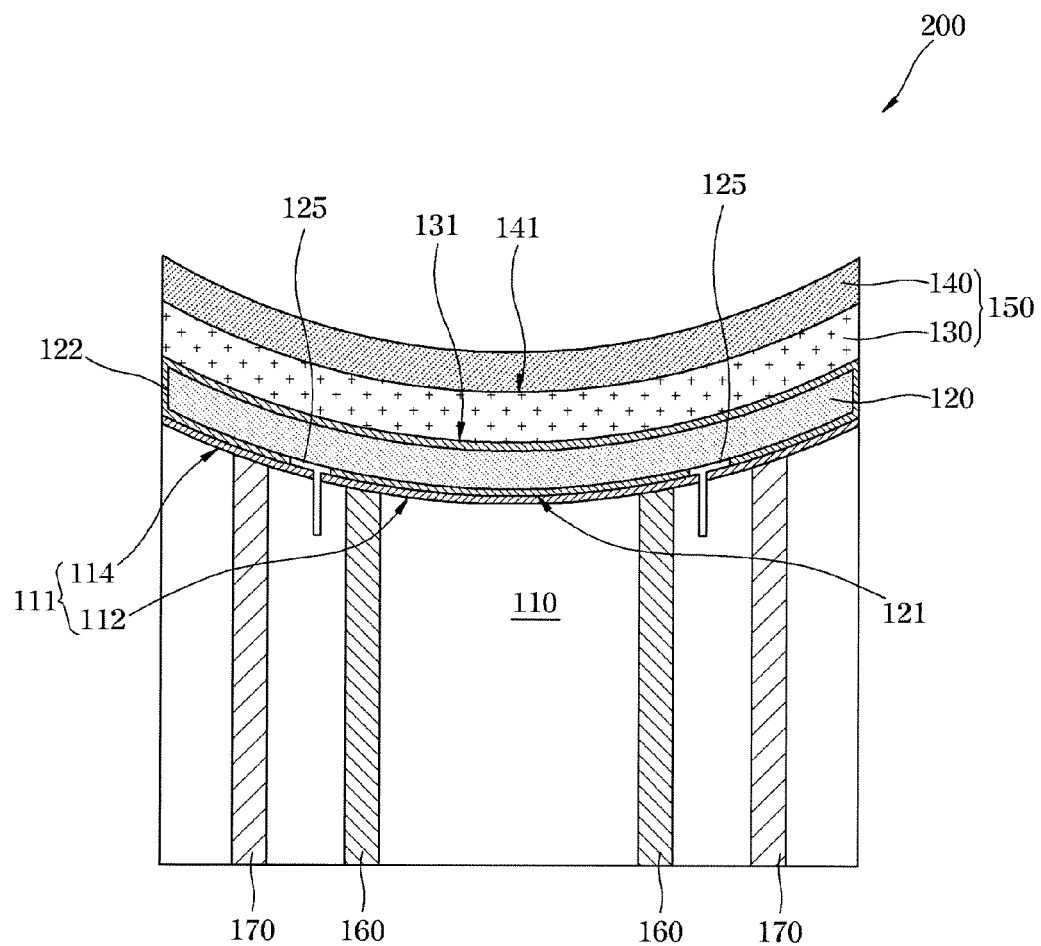
FIG. 4 is a side sectional view of a probe for an ultrasonic diagnostic apparatus according to another exemplary embodiment of the present disclosure.
Figure 5:
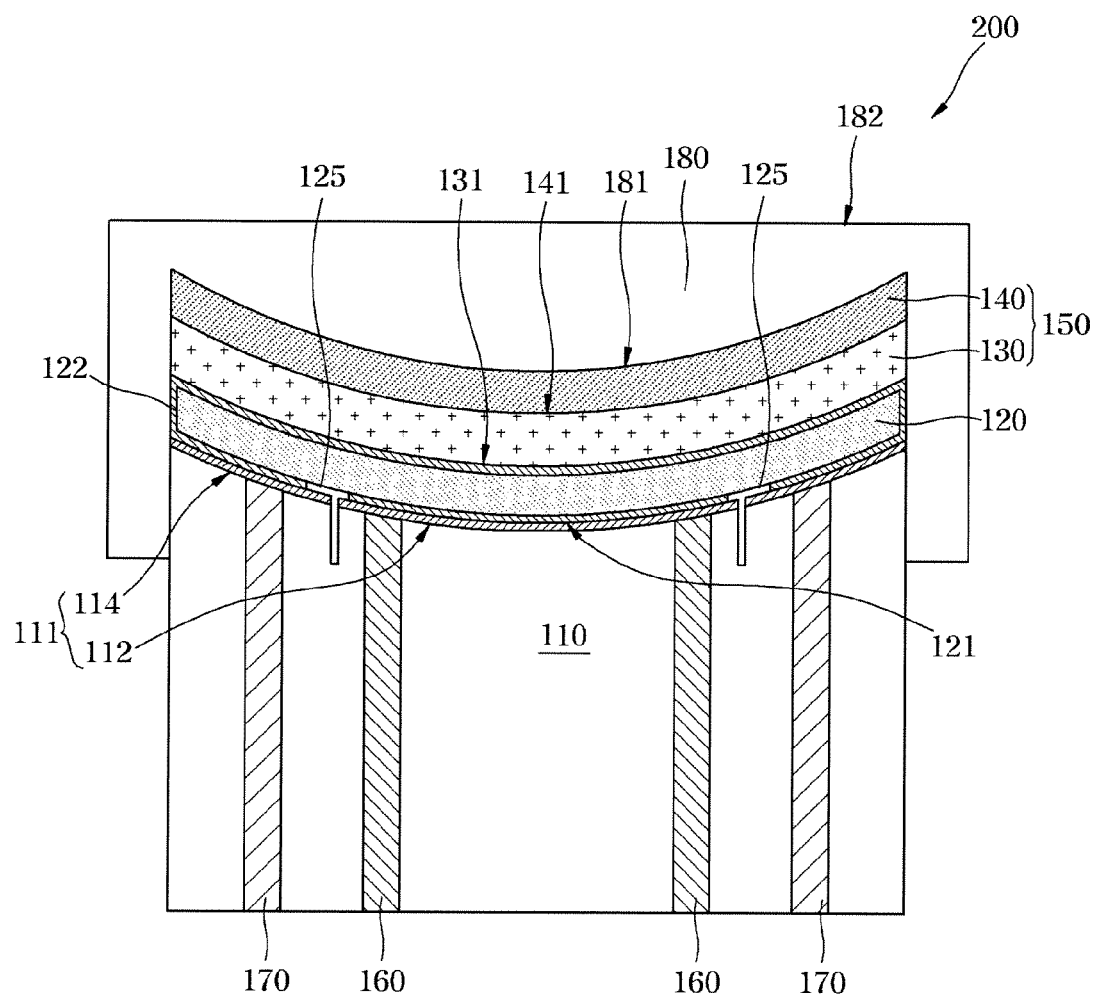
FIG. 5 is a side sectional view of a lens mounted on the probe of FIG. 4.
Figure 6:
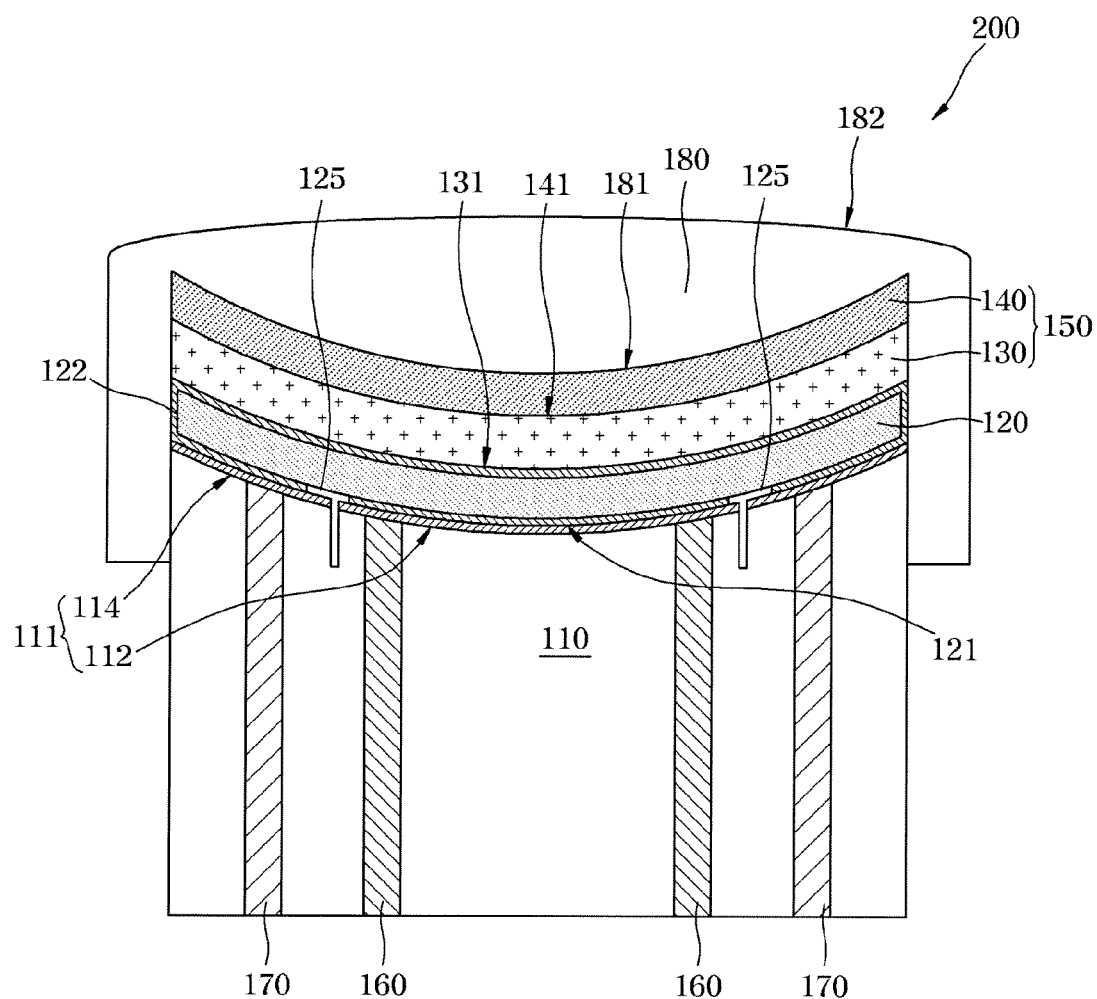
FIG. 6 is a side sectional view of a different lens mounted on the probe of FIG. 4.

FIG. 4 is a side sectional view of a probe for an ultrasonic diagnostic apparatus according to another exemplary embodiment, FIG. 5 is a side sectional view of a lens mounted on the probe of FIG. 4, and FIG. 6 is a side sectional view of a different lens mounted on the probe of FIG. 4.

For convenience of description, the same components as those of the embodiments shown in FIGS. 1 to 3 will be denoted by the same reference numerals, and a detailed description thereof will be omitted herein.

Referring to FIG. 4, a backing layer 110 of a probe 200 for an ultrasonic diagnostic apparatus according to this embodiment includes backing layer electrodes 111. A piezoelectric layer 120 is provided with a piezoelectric layer electrode 122 surrounding the piezoelectric layer 120 such that one side of the piezoelectric layer electrode 122 contacts the backing layer electrodes 111 and the other side of the piezoelectric layer electrode 122 contacts a matching layer 150. An insulator 125 is interposed between the backing layer electrodes 111 to divide the backing layer electrodes 111 into a first backing layer electrode 112 and a second backing layer electrode 114.

In this embodiment, a signal connector 160 is connected to the first backing layer electrode 112 and a ground connector 170 is connected to the second backing layer electrode 114. Further, the signal connector 160 and the ground connector 170 are disposed inside the backing layer 110 and extend in a different direction than the piezoelectric layer 120, as shown in FIG. 4.

According to this embodiment, the backing layer 110 is provided with the signal connector 160 therein and has a curved surface to allow a curved piezoelectric layer 120 to be mounted on the backing layer 110. Further, in this embodiment, the piezoelectric layer electrode 122 surrounds the piezoelectric layer 120 and the insulator 125 is interposed to divide the piezoelectric layer electrode 122 from the backing layer electrodes 111. As such, since the piezoelectric layer electrode 122 is formed to surround the piezoelectric layer 120, the signal connector 160 and the ground connector 170 may be disposed inside the backing layer 110 to permit electrical connection between components. Furthermore, since the piezoelectric layer electrode 122 surrounds the piezoelectric layer 120, the probe may eliminate an operation for bonding electrodes to the matching layer 150, thereby simplifying a manufacturing process.

As such, according to embodiments of the present disclosure, the probe for an ultrasonic diagnostic apparatus includes a stack of a backing layer, a piezoelectric layer and a matching layer, in which the piezoelectric layer is formed to have a certain curvature, thereby achieving performance improvement by minimization of interference from a signal connector and a ground connector.

In addition, in the case where a curved lens cannot be applied, the probe enables application of a planar lens and thus decreases the thickness of the lens, thereby improving sensitivity by inhibiting ultrasonic attenuation caused by the lens thickness, while preventing a problem of frequency drop. Accordingly, the probe according to the embodiment may be used as a high frequency probe.

Further, the probe includes a piezoelectric layer electrode configured to surround the piezoelectric layer and thus eliminates an operation for bonding electrodes to the matching layer, thereby simplifying a manufacturing process.

Further, in the probe for an ultrasonic diagnostic apparatus according to the embodiments, a signal connector and a ground connector may be bonded inside the backing layer, thereby eliminating a delicate manual soldering process. Thus, the probe allows easy connection of components, does not suffer from deterioration in performance caused by a connection failure between the components, and can prevent deterioration in performance of the piezoelectric layer caused by heat generation during manufacture of the probe.

Further, the signal connector and the ground connector are bonded inside the backing layer and electrically connected to the piezoelectric layer, instead of being disposed between the backing layer and the piezoelectric layer, so that the probe can prevent deterioration in performance caused by a connection failure between the piezoelectric layer and the signal connector and prevent damage of the ground connector or the signal connector.

Further, the signal connector and the ground connector are disposed inside the backing layer, thereby allowing separate manufacture or storage of the backing layer from other components of the probe. Accordingly, backing layers having various desired shapes and sizes may be manufactured and easily assembled with other components, thereby reducing manufacturing costs, facilitating manufacture of the probe, and improving uniformity of finished products.

Furthermore, the signal connector may be disposed near the ground connector, thereby reducing noise of the probe.

Although the present disclosure has been described with reference to the embodiments shown in the drawings, it should be understood by those skilled in the art that these embodiments are given by way of illustration only, and that various modifications, variations, and alternations can be made without departing from the spirit and scope of the present disclosure. The scope of the present disclosure should be limited only by the accompanying claims and equivalents thereof.

What is claimed is:

1. A probe for an ultrasonic diagnostic apparatus, comprising:
   a backing layer;
   a piezoelectric layer disposed on one side of the backing layer;
   a matching layer disposed on one side of the piezoelectric layer;
   a signal connector disposed inside the backing layer to transfer a signal to the piezoelectric layer; and a ground connector disposed outside the signal connector, wherein the backing layer, the piezoelectric layer and the matching layer are sequentially disposed and the signal connector is electrically connected to the piezoelectric layer at the other side of the piezoelectric layer, wherein the backing layer is provided with backing layer electrodes including first and second backing layer electrodes, the piezoelectric layer is provided with a piezoelectric layer electrode contacting the first backing layer electrodes, the matching layer is provided with a matching layer electrode contacting the piezoelectric layer electrode and the second backing layer electrode, and an insulator is provided between the backing layer electrodes to divide the backing layer electrodes into the first and second backing layer electrodes, wherein the signal connector and the ground connector are connected to the first and second backing layer electrodes, respectively, the signal connector and the ground connector being disposed inside the backing layer and extending in a different direction than a direction of the piezoelectric layer.

2. The probe according to claim 1, wherein the piezoelectric layer comprises a convex piezoelectric portion convexly formed towards the piezoelectric layer.

3. The probe according to claim 2, wherein the matching layer comprises a convex matching portion convexly formed corresponding to a shape of the convex piezoelectric portion.

4. The probe according to claim 3, further comprising: a lens disposed outside the matching layer and formed at one side thereof with a lens convex portion convexly formed corresponding to a shape of the convex matching portion.

5. The probe according to claim 4, wherein the other side of the lens opposite the lens convex portion is a planar surface.

6. The probe according to claim 4, wherein the other side of the lens opposite the lens convex portion is convex in a different direction from the lens convex portion.

7. The probe according to claim 1, wherein the signal connector and the ground connector are disposed only inside the backing layer.

* * * * *